United States Patent [19]

Jimenez

[11] Patent Number: 4,821,988
[45] Date of Patent: Apr. 18, 1989

[54] CATHETER BAG HOLDER

[76] Inventor: Louis M. Jimenez, P.O. Box 1916, Oroville, Calif. 95965-1916

[21] Appl. No.: 104,509

[22] Filed: Oct. 5, 1987

[51] Int. Cl.⁴ .............................................. A47G 29/00
[52] U.S. Cl. .................................. 248/227; 248/231.8
[58] Field of Search ............... 248/903, 227, 229, 230, 248/231.7, 231.8, 316.7, 360, 359 F, 359 R, 125; 24/343, 462; 5/503

[56] References Cited

U.S. PATENT DOCUMENTS

| | | | |
|---|---|---|---|
| 220,830 | 6/1871 | Harrison . | |
| 227,742 | 7/1873 | Logsdon . | |
| 722,349 | 3/1903 | Young | 248/227 |
| 1,187,845 | 6/1916 | Kolb | 5/503 |
| 1,230,438 | 6/1917 | Sloan | 248/343 |
| 1,687,795 | 10/1928 | Ritter | 248/343 |
| 2,155,097 | 4/1939 | Mendle | 248/125 |
| 3,194,526 | 7/1965 | Lemmond | 248/231.8 |
| 3,322,381 | 5/1967 | Bubb | 248/229 |
| 3,337,880 | 8/1967 | Florek | 248/285 X |
| 3,586,276 | 6/1971 | O'Mahoney | 248/359 F |
| 3,850,401 | 11/1974 | Snediker | 248/291 |
| 3,902,931 | 9/1975 | Danciger | 248/230 |
| 4,005,942 | 2/1977 | Shepherd | 248/125 |
| 4,616,797 | 10/1986 | Cramer | 248/230 |
| 4,666,111 | 5/1987 | Schuler | 248/231.7 |

*Primary Examiner*—J. Franklin Foss
*Assistant Examiner*—Robert A. Olson

[57] ABSTRACT

There is provided an elongated partly tubular clamp. Opened edges on the clamp are provided with flanges for ease in snapping the clamp to a bed frame or wheelchair support structure. A short rod with a hooked end extends horizontally from a flange on the closed side of the clamp when the clamp is snapped vertically to a vertical bed post or wheelchair frame. The assemblage is primarily for use as a catheter bag holder.

6 Claims, 2 Drawing Sheets

CATHETER BAG HOLDER

BACKGROUND OF THE INVENTION

1. Field of the Invention

This invention relates to snap-on clip support devices. My invention is designed to snap onto a vertical portion of a bedframe or wheelchair for the purpose of supporting a standard catheter bag.

2. Description of the Prior Art

Past art patents were examined from a search conducted in the following classes and subclasses:
248/230, 231.1, 316.7, 311.3, 227, 231.8, 229, D8/371, 354, 394, 395, 356, D6/462, 411, 418 and D20/43.

In a patent issued to B. Lemmmond on July 13, 1965, U.S. Pat. No. 3,194,526, a soap dish clamp is illustrated. A round rod must be available and the supported item, soap, would have to be light weight.

A patent issued to F. F. Florek, U.S. Pat. No. 3,337,880, dated Aug. 29, 1967, illustrates a spring biased clamp for supporting an intravenous bottle. Appears expensive and requires spring assistance to operate.

Two design patents show pliable material clamping devices: U.S. Pat. No. Des. 220,830, dated June 1, 1971, to B. Harrison, and U.S. Pat. No. Des. 227,742, issued to D. D. Logsdon on July 17, 1973. Both are lightly structured devices and not suitable use requirement of the present invention.

The pivotal support device of R. R. Snediker in U.S. Pat. No. 3,850,401, dated Nov. 26, 1974, requires a retainer bolt and would be inadequate for purposes similar to the catheter bag holder of this invention.

Other patents disclosing clamps included U.S. Pat. No. 3,902,931, dated Sept. 2, 1975 issued to Danciger et al; Pat. No. 4,616,797, Oct. 14, 1986, granted to Cramer; and U.S. Pat. No. 4,666,111, to Schuler, dated May 19, 1987. The latter patents were not similar to the present invention.

To my knowledge, the foregoing patents were the most pertinent to my invention and no clamping devices seen by me would appear to interfere with further prosecution of the present application.

SUMMARY OF THE INVENTION

In practicing my invention, I have supplied a partly tubular clamp with angled edges for ease in snapping to a bed frame or to wheelchair support structure. A metal embodiment of the invention uses a flanged edge to strongly support an extended hook rod as is required to hold up a catheter bag. In a plastic embodiment, a lengthened half tubular clamping member supports an extended plastic hook. The hook is braced by a solid right angle support member.

A primary object of the invention is to provide an easily attachable clamp affixed with a hook rod for safely supporting a catheter bag.

Another object of my invention is to provide a hook support for catheter bags which can be used clamped to a bed frame or to the supports of a wheelchair.

A further object of this invention is to provide a catheter bag holder which is easy to manufacture of either metal or plastic.

A still further object of my invention is to provide a snap-on clamping device for supporting a catheter bag where the clamp is of sufficient length and strength so that no screw or bolt is required to retain the clamp.

Other objects and the many advantages of this invention will be understood by a reading of the numbered parts in the specification and comparing them with similar numbered parts shown on the included drawings.

DRAWING REFERENCE NUMERALS

Figures 1, 2, 3:
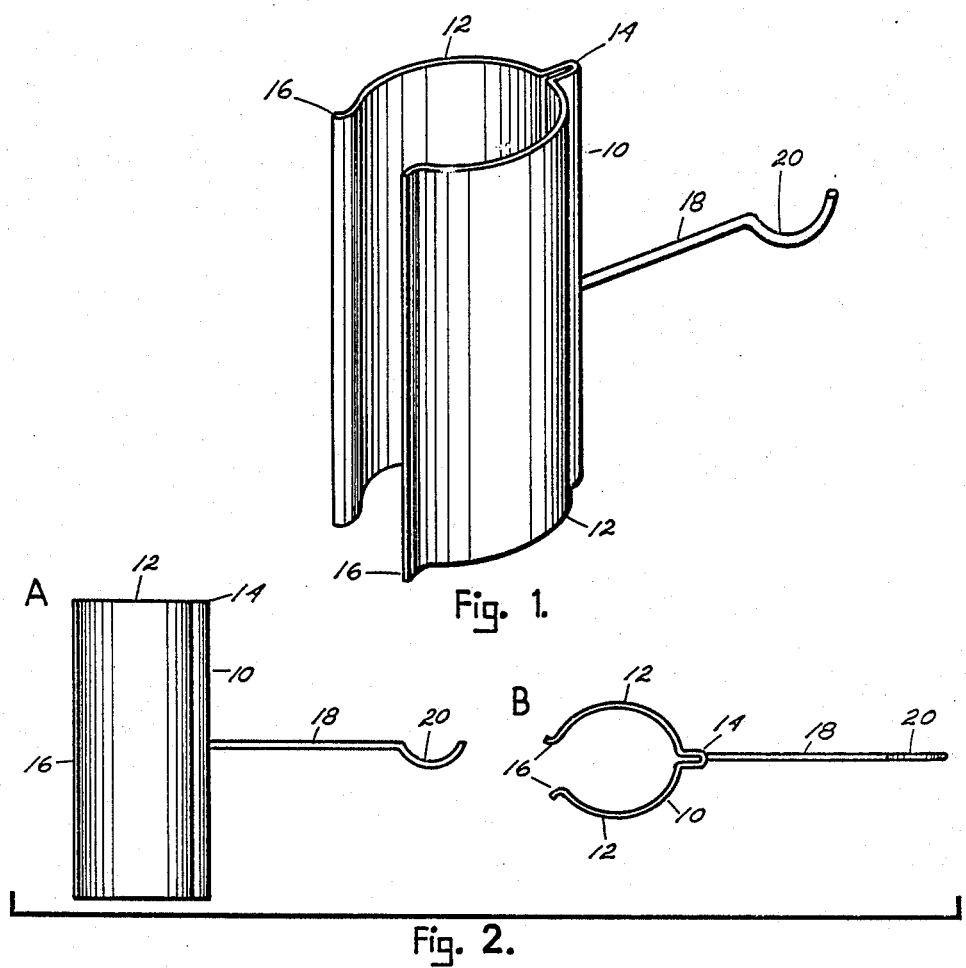
FIG. 1 is a perspective view of the metallic embodiment of the catheter bag holder.
FIG. 2 shows reduced drawings of the metallic catheter bag holder with A illustrating FIG. 1 in a side view and B showing the metallic catheter bag holder of this invention in a top plan view.
FIG. 3 shows the catheter bag holder clamped to a bed post and in use supporting a catheter bag.

DRAWING REFERENCE NUMERALS 10 metallic embodiment
12 curved longitudinal side wall
14 hook rod support
16 flared flange
18 metallic hook rod
20 metallic hook
22 bed
24 bed post
26 catheter bag
28 catheter bag support cord
30 catheter tubing
32 catheter drain plug
34 plastic embodiment
36 plastic hook support ridge
38 plastic hook support bracket
40 hook support frame member
42 plastic hook
44 wheelchair
46 wheelchair frame

DESCRIPTION OF THE PREFERRED EMBODIMENT

Referring now to the drawings at FIG. 1 and FIG. 2 where the metallic embodiment of the catheter bag holder is illustrated. The metallic embodiment 10 of the clamp assemblage is shown in a perspective view in FIG. 1, in a reduced side view at A of FIG. 2 and in a reduced plan view at B. Curved longitudinal side walls 12 are substantially three quarters tubular with flared flanges 16 as clamp terminal ends. Flared flanges 16 assist in positioning curved longitudinal side walls 12 for easy attachment. The extended length of curved longitudinal side walls 12 plus the type of resilient material used for manufacture make this structure a reliable attachment to hold a catheter bag. Additional strength is manufactured into metallic embodiment 10 by hook rod support 14 along the back of the clamp. The positive retention of metallic hook rod 18 by hook rod support 14 makes metallic hook 20 a reliable support for the catheter bag. In FIG. 3, metallic embodiment of the clamp and hook are shown in use. Guided by flared flanges 16, curved longitudinal side wall are firmly attached to bed post 24. Catheter bag 26 is held by catheter bag support cord 28 to metallic hook 20. Metallic embodiment 10 can be adjusted on bed post 24 to a position so catheter drain 32 is clear of the floor. Metallic hook rod 18 holds catheter bag 26 sufficiently clear of bed 22.

Figure 4:
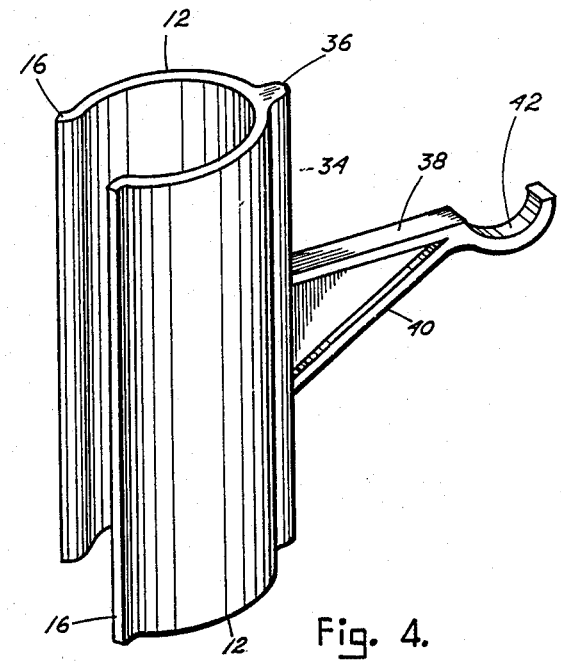
FIG. 4 is a perspective view of the plastic embodiment of the catheter bag holder.
Figure 5:
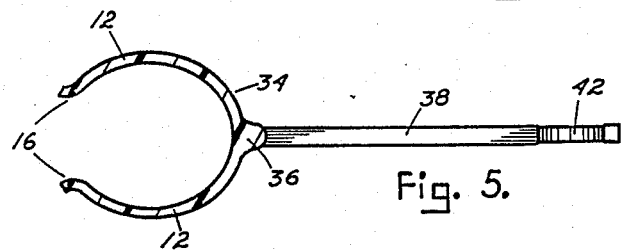
FIG. 5 shows the plastic embodiment of my catheter bag holder in a top plan view.

FIG. 4 shows plastic embodiment 34 of the catheter bag holder. A reinforced plastic hook 42 is supported by plastic hook support frame 38 in part with angled hook support frame 40. Frame 38 and hook support frame member 40 form a triangle which is filled of a solid panel for added strength. Flared flanges 16 again act as guides and leaders for snapping curved longitudinal side wall 12 to a bed post or wheelchair frame. FIG. 5 illustrates plastic embodiment 34 of the catheter holder in a top plan view.

Figure 6:
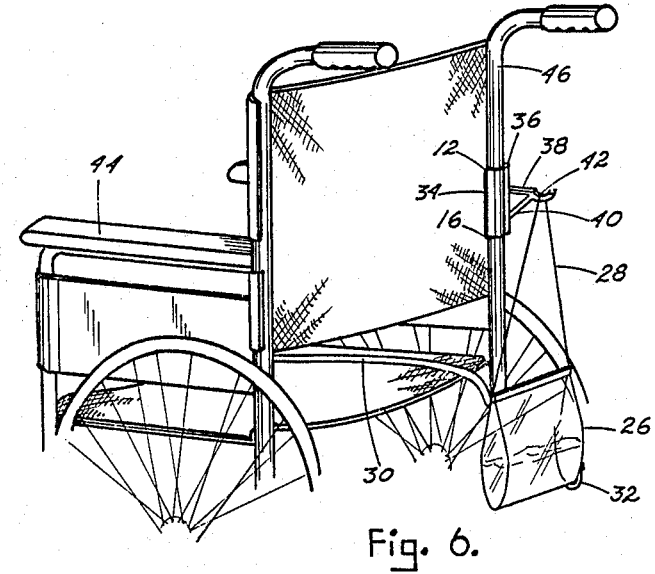
FIG. 6 illustrates the plastic embodiment of the invention in use clamped to the frame of a wheelchair.

In use on wheelchair 44 as shown in FIG. 6, plastic embodiment 34 of my holder is illustrated attached to wheelchair frame 46. Plastic hook 42 is extended sufficiently from plastic hook support ridge 36 to support catheter bag 26 on catheter bag support cord 28 so catheter drain 32 is clear of wheelchair frame 46. Catheter tubing 30 can be run over, as illustrated, or under the chair seat of wheelchair 44.

Although I have described my invention with considerable details in the specification, it is to be understood that modifications in the design and structure of the embodiments of the device may be practiced which do not depart from the intended scope of the appended claims.

What is claimed is:

1. A catheter bag holder, comprising:
   in a metallic embodiment, an elongated tubular member opened longitudinally along one side with the edges thereof flanged outwardly providing a clamp structured for removable snap-on attachment to a bed rail, a wheelchair frame, and the like;
   a hook rod support, said hook rod support being a narrow ridge diametrically rounded formed by a longitudinal wall continuation of said clamp aligned full length therein oppositely said opened side of said clamp;
   a hook rod, said hook rod being affixed to said hook rod support ridge right angled outwardly from said clamp oppositely said opened side, said hook rod formed at the free end with an opened hook, said opened hook sized for attachment as a holder to the support cord of said catheter bag and said hook rod of minimal length required to support said catheter bag usefully.

2. The catheter bag holder of claim 1, wherein said tubular member of said clamp being fabricated of a metallic material having sufficient pliability to allow widening of said opening for engagement of said bed rail, said wheelchair frame, and said like, and having sufficient resilience to return firmly to an original position.

3. The catheter bag holder of claim 1, wherein said hook rod is fabricated of a metallic material having sufficient tensile strength to maintain said catheter bag suspended usefully.

4. A catheter bag holder, comprising:
   in a plastic embodiment, an elongated tubular member opened longitudinally along one side with the edges thereof flanged outwardly providing a clamp structured for removable snap-on attachment to a bed rail, a wheelchair frame, and the like;
   a plastic hook support, said hook support being a diametrically rounded narrow ridge of solid plastic structure formed longitudinally and molded full length in said tubular member of said clamp as an integral part thereof with said hook support ridge protruding outwardly oppositely said opening in said tubular member;
   a plastic hook support bracket affixed right angled to said plastic hook support ridge, said bracket having an extending free end, there being an angled hook support frame member affixed upwardly adjacent said extending free end and downwardly to said hook support ridge with said hook support ridge, said hook support bracket, and said angled hook support frame member substantially forming a triangle encompassing paneling;
   a plastic hook, said plastic hook being a loop formed into said extending free end of said plastic hook support bracket providing an opened hook, said opened hook sized for attachment as a holder to the support cord of said catheter bag with said extending free end forming said opened hook of minimal length required to support said catheter bag usefully.

5. The catheter bag holder of claim 4, wherein said tubular member of said clamp being fabricated of a plastic material having sufficient pliability to allow widening of said opening for engagement of said bed rail, said wheelchair frame, and said like, and having sufficient resilience to return firmly to an original position.

6. The catheter bag holder of claim 4, wherein said plastic hook support bracket, said plastic hook, said downwardly angled hook support frame member, and said encompassed paneling being fabricated of a plastic material of sufficient tensile strength to maintain said catheter bag suspended usefully.

* * * * *